US008625868B2

(12) United States Patent
Takayama et al.

(10) Patent No.: US 8,625,868 B2
(45) Date of Patent: Jan. 7, 2014

(54) RADIATION DIAGNOSTIC APPARATUS AND IMAGE RECONSTRUCTING METHOD

(75) Inventors: Takuzo Takayama, Otawara (JP); Manabu Teshigawara, Otawara (JP); Kenta Moriyasu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 628 days.

(21) Appl. No.: 12/880,506

(22) Filed: Sep. 13, 2010

(65) Prior Publication Data

US 2011/0064293 A1 Mar. 17, 2011

(30) Foreign Application Priority Data

Sep. 14, 2009 (JP) ................................. 2009-212270
Aug. 23, 2010 (JP) ................................. 2010-186578

(51) Int. Cl.
*G06K 9/00* (2006.01)
(52) U.S. Cl.
USPC ............... 382/131; 382/128; 382/132; 378/1; 378/2; 378/4; 250/362; 250/363.01; 250/363.02; 250/363.03
(58) Field of Classification Search
None
See application file for complete search history.

(56) References Cited

U.S. PATENT DOCUMENTS

| 5,751,837 | A | * | 5/1998 | Watanabe et al. ............. 382/131 |
| 6,185,272 | B1 | * | 2/2001 | Hiraoglu et al. ................ 378/57 |
| 7,349,520 | B2 | | 3/2008 | Nakashima |
| 7,961,840 | B2 | | 6/2011 | Ohi et al. |
| 2002/0011571 | A1 | * | 1/2002 | Lin et al. ........................ 250/366 |
| 2002/0179843 | A1 | * | 12/2002 | Tanaka et al. ............. 250/363.03 |
| 2008/0056432 | A1 | * | 3/2008 | Pack et al. .......................... 378/4 |
| 2008/0056435 | A1 | * | 3/2008 | Basu et al. ......................... 378/9 |
| 2008/0056436 | A1 | * | 3/2008 | Pack et al. ....................... 378/10 |
| 2009/0245457 | A1 | * | 10/2009 | Takeuchi et al. .................. 378/8 |

FOREIGN PATENT DOCUMENTS

| CN | 1615800 A | 5/2005 |
| WO | WO 2008/081525 A1 | 7/2008 |

OTHER PUBLICATIONS

"Medical Image/Radiological Equipment Hand Book." Japan Industries Association of Radiological Systems. Nago Bijutsu Insatsu Kabushiki Kaisha. 2001. 3 pages. (with Partial English Translation).
Chinese Office Action issued Jun. 25, 2012, in China Patent Application No. 201010284253.8.

* cited by examiner

*Primary Examiner* — Matthew Bella
*Assistant Examiner* — Jason Heidemann
(74) *Attorney, Agent, or Firm* — Oblon, Spivak, McClelland, Maier & Neustadt, L.L.P.

(57) ABSTRACT

According to one embodiment, a radiation diagnostic apparatus includes a photon-counting detector, a counting information storage unit, an image reconstituting unit, and a controlling unit. The detector performs counting on light derived from incident radiation. The counting information storage unit stores therein counting information based on the counting result of the detector. The image reconstituting unit reconstitutes a medical image by performing a back projection process on projection data that is generated by use of the counting information stored in the counting information storage unit. After the reconstitution of the medical image, the controlling unit performs control so that all or part of the counting information is maintained in the counting information storage unit.

12 Claims, 8 Drawing Sheets

FIG.3

| MODULE ID | P | E | T |
|---|---|---|---|
| D1 | P11 | E11 | T11 |
|  | P12 | E12 | T12 |
|  | P13 | E13 | T13 |
|  | ⋮ | ⋮ | ⋮ |

| MODULE ID | P | E | T |
|---|---|---|---|
| D2 | P21 | E21 | T21 |
|  | P22 | E22 | T22 |
|  | P23 | E23 | T23 |
|  | ⋮ | ⋮ | ⋮ |

| MODULE ID | P | E | T |
|---|---|---|---|
| D3 | P31 | E31 | T31 |
|  | P32 | E32 | T32 |
|  | P33 | E33 | T33 |
|  | ⋮ | ⋮ | ⋮ |

COINCIDENCE COUNTING INFORMATION
GENERATING CONDITIONS

TIME WINDOW WIDTH: 600 psec
ENERGY WINDOW WIDTH: 350 keV TO 550 keV
.
.
.

FIG.4B

| P11 | E11 | T11 | P22 | E22 | T22 |
|-----|-----|-----|-----|-----|-----|
| P12 | E12 | T12 | P32 | E32 | T32 |
| P13 | E13 | T13 | P33 | E33 | T33 |
| ⋮ | ⋮ | ⋮ | ⋮ | ⋮ | ⋮ |

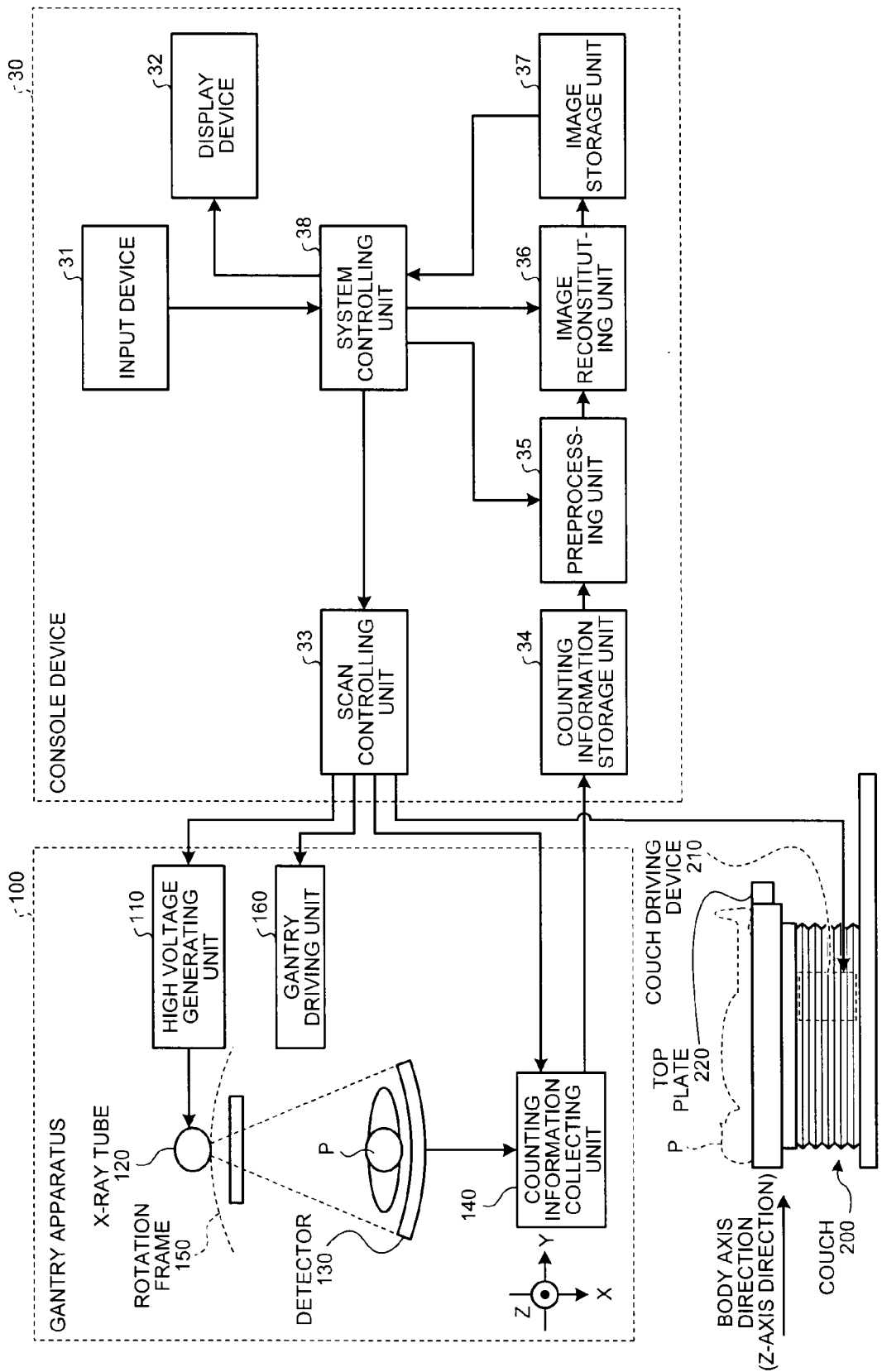

FIG.7

| TUBE PHASE | P | E |
|---|---|---|
| X1 | P11 | E11 |
| | P12 | E12 |
| | P13 | E13 |
| | ⋮ | ⋮ |

| TUBE PHASE | P | E |
|---|---|---|
| X2 | P21 | E21 |
| | P22 | E22 |
| | P23 | E23 |
| | ⋮ | ⋮ |

| TUBE PHASE | P | E |
|---|---|---|
| X3 | P31 | E31 |
| | P32 | E32 |
| | P33 | E33 |
| | ⋮ | ⋮ |

⋮

RADIATION DIAGNOSTIC APPARATUS AND IMAGE RECONSTRUCTING METHOD

CROSS-REFERENCE TO RELATED APPLICATIONS

This application is based upon and claims the benefit of priority from Japanese Patent Application No. 2009-212270, filed on Sep. 14, 2009, and Japanese Patent Application No. 2010-186578, filed on Aug. 23, 2010; the entire contents of all of which are incorporated herein by reference.

FIELD

Embodiments described herein relate generally to a radiation diagnostic apparatus and an image reconstructing method.

BACKGROUND

Conventionally, a positron emission computed tomography (PET) apparatus and an X-ray computed tomography (X-ray CT) apparatus have been known as a radiation diagnostic apparatus that use radiation. Such a radiation diagnostic apparatus presents images created on the basis of its own characteristics, and thereby realizes image diagnosis essential to today's medical practice.

A PET apparatus is one of nuclear medicine diagnostic devices, which offers detailed functional information on human body tissue in the form of images. More specifically, when a drug labeled with positron emitting radionuclides are introduced to a subject and positrons emitted from the introduced drug are bound to electrons and annihilated, the PET apparatus conducts coincidence counting on a pair of 511-keV gamma rays that are emitted substantially in opposite directions, by use of a detector having photon-counting detector modules arranged around the subject in the form of a ring. Then, the PET apparatus performs computations on the coincidence counting data of the gamma rays, and thereby reconstructs an image (PET image) that shows the distribution of the human body tissue into which the drug is introduced.

The coincidence counting process performed by the PET apparatus is now explained. First, in the PET apparatus, multiple Anger-type detector modules that each include scintillators in which NaI, BGO and the like are two-dimensionally aligned to convert the incident gamma rays to visible light and multiple photomultiplier tubes (PMTs) densely arranged by way of a light guide are arranged in the form of a ring (for example, see "Medical Image/Radiological Equipment Hand Book" edited by Japan Industries Association of Radiological Systems, published by Nago Bijutsu Insatsu Kabushiki Kaisha, 2001, pp. 190-191). The light guide is made of a light transmissive plastic or the like and used to transfer the visible light output by the scintillators to the PMTs. The PMTs multiply the visible light output by the scintillators and convert it to electric signals.

A coincidence circuit connected to the PMTs of each detector module generates coincidence counting information based on the results output by each detector module to determine the incident direction of a pair of gamma rays that are emitted from the positrons. More specifically, the coincidence circuit determines the incident position of the gamma rays in the detector module (i.e., the position of the scintillator) by calculating the position of the center of gravity from the positions of the PMTs that convert the visible light scattered from the scintillator to electric signals at the same timing and output the signals and the energy of the incident gamma rays corresponding to the intensity of the electric signals. In addition, the coincidence circuit integrates the intensity of the electric signal output by each PMT, and thereby calculates the energy value of the gamma ray that is incident on the detector module.

Then, the coincidence circuit performs a search (coincidence finding) for a combination of the results output by the detector modules, for example, in which the incident timing of the gamma ray falls within a specific time window width (e.g., 2 nanoseconds) and the energy values are within a specific energy window width (e.g., 350 keV to 550 keV). Then, the coincidence circuit generates coincidence counting information (coincidence list) as coincidentally counting information of two annihilation photons. Then, the PET apparatus uses the generated coincidence counting information as projection data (sinogram data), and reconstitutes a PET image by performing a back projection process on the projection data. In the coincidence circuit, random corrections can be made by use of a count ratio (count/sec) to eliminate the random coincidence that is included stochastically at a certain rate.

On the other hand, the X-ray CT apparatus is one of transmission CT apparatus, which offers detailed morphological information of human body tissue. More specifically, in the X-ray CT apparatus, the subject is irradiated with x rays from multiple directions by rotating the x-ray tube and the current-mode measuring detector in pair around the body axis of the subject, and the detector measures the intensity in different directions of the x rays that have been absorbed and attenuated when passing through the body. Then, by performing the back projection process on the projection data generated from the x-ray intensity distribution obtained by the detector, an X-ray CT image showing the morphological information of the human body tissue of the subject is reconstituted.

Moreover, recently, in the X-ray CT apparatus, a photon-counting CT that incorporates a photon-counting detector used in a PET apparatus or the like, in place of a conventional current-mode measuring detector, has been developed. In the photon-counting CT, each detection element of the photon-counting detector executes counting of the energy value of the X-rays that pass through the subject, and therefore a spectrum from which elements that constitute the body tissue of the X-rayed subject can be estimated can be prepared as projection data, and therefore an X-ray CT image describing differences in element level can be generated.

With a conventional PET apparatus, however, coincidence counting information generated only by a coincidence circuit that is a piece of hardware can be stored, which means that no coincidence counting information with a modified time window width or energy window width can be regenerated. In other words, with the conventional PET apparatus, the results output by detector modules are abandoned if they are determined as not coincident. For this reason, if a PET image needs to be corrected in response to a request from a reader of the PET image, for example, that the PET image should be reconstituted with a modified time window width or energy window width, a PET image has to be newly taken.

Furthermore, with the above photon-counting CT, only projection data is stored, but the counting result obtained by the photon-counting detector is not stored. Thus, image corrections such as scattered radiation corrections cannot be made by use of the counting results of the detector in response to a request from the reader of an x-ray CT image.

With the above conventional technologies, a medical image that is reconstituted by use of radiation cannot be quickly corrected in response to a request from a reader.

BRIEF DESCRIPTION OF THE DRAWINGS

FIG. 3 is a diagram for explaining the counting information storage unit according to the first embodiment;

FIGS. 4A and 4B are diagrams for explaining a coincidence counting information generating unit;

FIG. 6 is a diagram for explaining a configuration of an X-ray CT apparatus according to a second embodiment;

FIG. 7 is a diagram for explaining a counting information storage unit according to the second embodiment;

DETAILED DESCRIPTION

In one embodiment, a radiation diagnostic apparatus includes a photon-counting detector, a counting information storage unit, an image reconstituting unit, and a controlling unit. The detector performs counting on light derived from incident radiation. The counting information storage unit stores therein counting information based on the counting result of the detector. The image reconstituting unit reconstitutes a medical image by performing a back projection process on projection data that is generated by use of the counting information stored in the counting information storage unit. After the reconstitution of the medical image, the controlling unit performs control so that all or part of the counting information is maintained in the counting information storage unit.

Embodiments of the radiation diagnostic apparatus are now explained in detail with reference to the attached drawings. The radiation diagnostic apparatus refers to a medical diagnostic imaging apparatus that reconstitutes a medical image by use of radiation. In the explanation of the first embodiment, the image reconstructing method employed by a positron emission computed tomography (PET) apparatus as a radiation diagnostic apparatus is dealt with, and in the explanation of the second embodiment, the image reconstructing method employed by an X-ray computed tomography (CT) apparatus as a radiation diagnostic apparatus is dealt with.

The PET apparatus performs coincidence counting on a pair of gamma rays emitted from body tissue to which positron emitting radionuclides given to the subject are introduced, and thereby reconstitutes a PET image showing the distribution of the body tissue to which the positron emitting radionuclides are introduced. Then, the PET apparatus according to the first embodiment is configured to quickly correct the PET image in response to a request from the reader.

Figure 1:
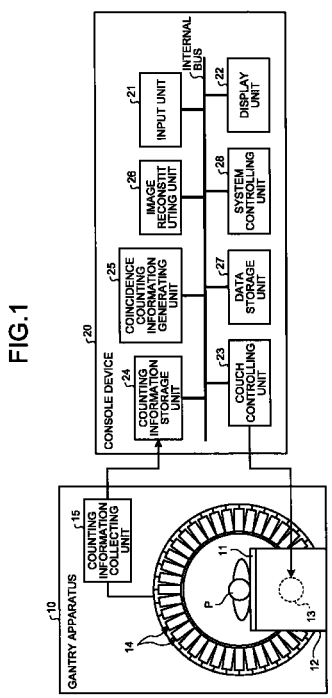
FIG. 1 is a diagram for explaining a configuration of a PET apparatus according to a first embodiment.

The configuration of the PET apparatus according to the first embodiment is now explained with reference to FIG. 1 and the like. FIG. 1 is a diagram for explaining a configuration of a PET apparatus according to a first embodiment. The PET apparatus according to the first embodiment includes a gantry apparatus 10 and a console device 20.

The gantry apparatus 10 executes counting during a predetermined monitoring period onto pairs of gamma ray emitted from the positron emitting radionuclides that are introduced to a subject P and selectively taken into the living tissue of the subject P. The gantry apparatus 10 includes a top plate 11, a couch 12, a couch driving unit 13, detector modules 14, and a counting information collecting unit 15. The gantry apparatus 10 has an opening, which serves as an imaging space as illustrated in FIG. 1.

The top plate 11 is a bed on which the subject P lies, and arranged on top of the couch 12. The couch driving unit 13 moves the couch 12 under the control of a couch controlling unit 23, which will be described later, and thereby carries the subject P into the imaging space of the gantry apparatus 10.

The detector modules 14 are photon-counting detectors that detect gamma rays emitted from the subject P. In the gantry apparatus 10, multiple detector modules 14 are arranged in the form of a ring to surround the subject P.

Figure 2A:
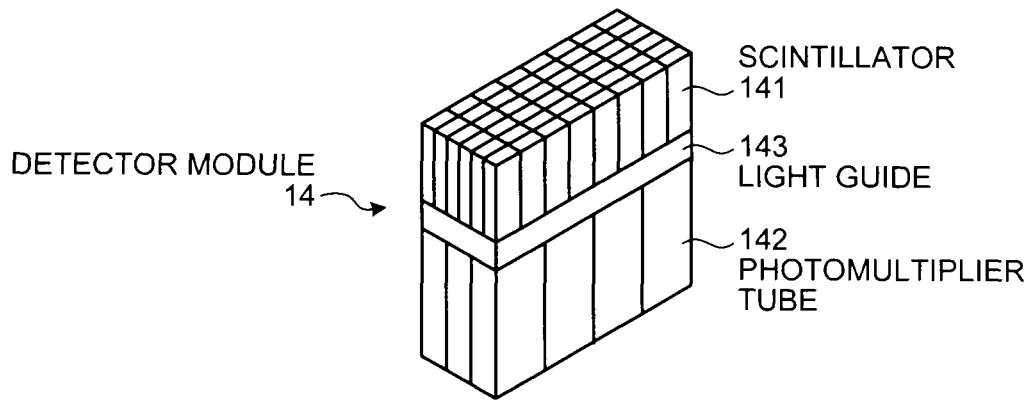
FIGS. 2A and 2B are diagrams for explaining the detector module and the counting information collecting unit according to the first embodiment.
Figure 2B:
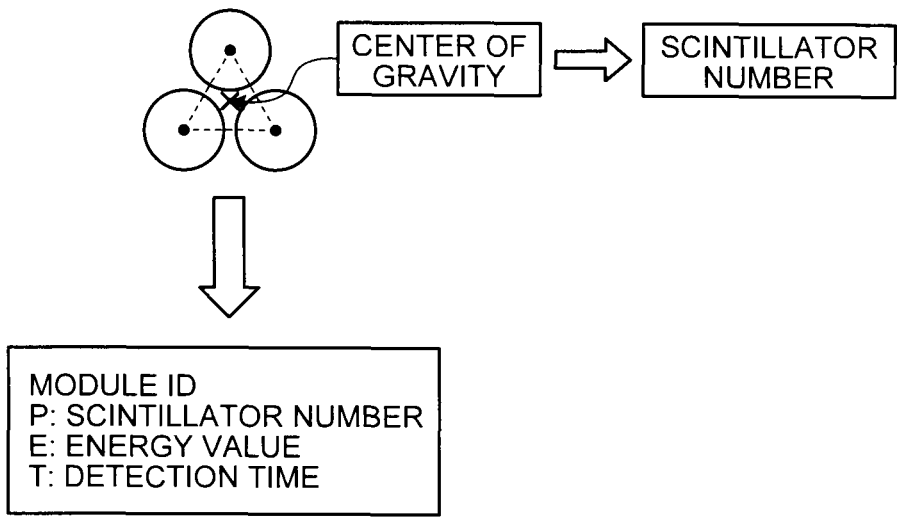

More specifically, as illustrated in FIG. 2A, a detector module 14 is an Anger-type detector that includes scintillators 141, photomultiplier tubes 142 (PMTs), and a light guide 143. FIGS. 2A and 2B are diagrams for explaining the detector module and the counting information collecting unit according to the first embodiment.

The scintillators 141 are, as illustrated in FIG. 2A, two-dimensionally aligned NaI, BGO, and the like that is to convert the incident gamma rays emitted from the subject P to visible light. Furthermore, the photomultiplier tubes 142 multiply the visible light output by the scintillators 141 and convert it to an electrical signal. As illustrated in FIG. 2A, the multiple photomultiplier tubes 142 are densely arranged by way of the light guide 143. The light guide 143 is used to transfer the visible light output by the scintillators 141 to the photomultiplier tubes 142, and is formed of a plastic material or the like with excellent optical transmission characteristics.

The photomultiplier tubes 142 have a photocathode that receives scintillation light and generates photoelectrons, multistage dynodes that provide an electric field for accelerating the generated photoelectrons and an anode that is an outlet of the electrons. With the photoelectric effect, the electrons emitted from the photocathode are accelerated toward the dynodes and collide against the surface of the dynodes, throwing multiple electrons out. Because this phenomenon is repeated over the multistage dynodes, the number of electrons is multiplied in the form of avalanche, reaching approximately one million at the end of the anode. In this example, the gain ratio of the photomultiplier tubes 142 is one millionfold. Because of the amplification using the avalanche phenomenon, a voltage of 1000 volts or higher is usually applied between the dynodes and the anode.

In other words, the detector modules 14 counts the number of gamma rays emitted from the subject P by converting the gamma rays into visible light at the scintillators 141 and converting the converted visible light to electric signals at the electronic photomultiplier tubes 142.

In FIG. 1, the counting information collecting unit 15 collects the counting results obtained by each of the detector modules 14, as counting information. More specifically, the counting information collecting unit 15 collects, for each detector modules 14, the detection position of the gamma ray detected by the detector module 14, the energy value of the gamma ray at the incident time to the detector module 14, and the detection time of the gamma ray at the detector module 14, as counting information based on the counting results obtained by the detector module 14, and transmits the collected counting information to the console device 20.

First, the counting information collecting unit 15 performs an Anger-type position calculating process to collect the detection position from the counting results of the detector modules 14. Alternatively, when the photomultiplier tubes 142 are position-detecting photomultiplier tubes, the counting information collecting unit 15 performs collection of the detection position at the position-detecting photomultiplier tubes. In particular, as illustrated in FIG. 2B, the counting information collecting unit 15 calculates the position of the center of gravity from the positions of the photomultiplier tubes 142 that convert and output scintillation light of the scintillators 141 to electrical signals at the same timing and the gamma ray energy value corresponding to the intensities of the electrical signals, and thereby determines the scintillator number (P) designating the incident position of the gamma ray to the scintillator. Furthermore, the counting information collecting unit 15 integrates the intensity of the electrical signal output by each photomultiplier tube 142, and thereby determines the energy value (E) of the gamma ray incident to the detector module. The counting information collecting unit 15 also collects the detection time (T) at which the detector modules 14 detect the gamma ray.

The detection time (T) may be an absolute time (clock time) or a relative time with respect to the PET imaging start time. The counting information collecting unit 15 collects the detection time (T) with precision to $10^{-12}$ seconds (picoseconds). With such a process, the counting information collecting unit 15 collects, as counting information, "P: scintillator number", "E: energy value" and "T: detection time" that identify a detector module 14 in correspondence with a "module ID", as illustrated in FIG. 2B.

In FIG. 1, the console device 20 receives operations of the PET apparatus from the operator and reconstitutes a PET image from the counting information collected by the gantry apparatus 10.

More specifically, the console device 20 includes, as illustrated in FIG. 1, an input unit 21, a display unit 22, a couch controlling unit 23, a counting information storage unit 24, a coincidence counting information generating unit 25, an image reconstituting unit 26, a data storage unit 27, and a system controlling unit 28. The units of the console device 20 are connected to one another by way of an internal bus.

The input unit 21 includes a mouse, a keyboard and the like that the operator of the PET apparatus uses to input various instructions and settings, and sends the instruction and setting information received from the operator to the system controlling unit 28. For example, the input unit 21 receives reconstitution conditions for reconstituting the PET image and correction conditions for correcting the image from the operator.

The display unit 22 is a monitor that the operator checks. Under the control of the system controlling unit 28, the display unit 22 presents a PET image to the operator, and displays a graphical user interface (GUI) to receive various instructions and settings from the operator by way of the input unit 21.

The couch controlling unit 23 controls the couch driving unit 13 so that the subject P is carried into the imaging space of the gantry apparatus 10.

The counting information storage unit 24 stores therein the counting information collected by the counting information collecting unit 15 for each detector module 14. For example, the counting information storage unit 24 stores therein, as illustrated in FIG. 3, "P: P11, E: E11, T: T11" and "P: P12, E: E12, T: T12" as counting information collected by the detector module 14 of "module ID: D1" from the counting results. FIG. 3 is a diagram for explaining the counting information storage unit according to the first embodiment, in which "P", "E", and "T" refer to "scintillator number", "energy value", and "detection time".

Furthermore, the counting information storage unit 24 stores therein, as illustrated in FIG. 3, the counting information collected from the counting results by the detector modules 14 of "module ID: D2" and "module ID: D3", in the same manner as the above.

In FIG. 1, the coincidence counting information generating unit 25 searches for a combination of counting information items in which a pair of gamma rays emitted from the positron emitting radionuclides are coincidentally counted, based on at least the detection times of the counting information stored in the counting information storage unit 24. Then, the coincidence counting information generating unit 25 generates coincidence counting information from the detected combination of the counting information items that is to determine the incident direction of the pair of gamma rays emitted from positrons. The coincidence counting information generated by the coincidence counting information generating unit 25 is used as the projection data for the process performed by the image reconstituting unit 26, which will be described later.

In particular, the coincidence counting information generating unit 25 generates the coincidence counting information, based on coincidence counting information generating conditions contained in the reconstituting conditions input by the operator by way of the input unit 21. Here, the coincidence counting information generating conditions designate, for example, the time window width and the energy window width. For example, the coincidence counting information generating unit 25 generates the coincidence counting information by use of the coincidence counting information generating conditions "time window width: 600 picoseconds, energy window width: 350 keV to 550 keV" designated by the operator, as illustrated in FIG. 4A. FIGS. 4A and 4B are diagrams for explaining the coincidence counting information generating unit.

In particular, the coincidence counting information generating unit 25 refers to "detection times (T)" and "energy values (E)" for each module ID illustrated in FIG. 3, and searches for a combination of counting information items among the modules, in which a difference in the detection times is within "time window width: 600 picoseconds" and the energy values are both within "energy window width: 350 keV to 550 keV".

In this manner, the coincidence counting information generating unit 25 generates coincidence counting information of two coincidentally counted annihilation photons, for example, from a combination of "P: P11, E: E11, T: T11" and "P: P22, E: E22, T: T22", as illustrated in FIG. 4B.

Then, the coincidence counting information generating unit 25 stores the generated coincidence counting information as the projection data (sinogram data) of the subject P in the data storage unit 27.

In addition to the time window width and the energy window width, the operator is allowed to incorporate, in the coincidence counting information generating conditions, parameters such as for random corrections for excluding a random coincidence, scattering corrections for excluding the counting information of the scattered gamma rays from the coincidence counting information, sensitivity corrections for correcting a difference in the sensitivities of the detector modules 14, and attenuation corrections for correcting the energy value of the gamma rays that are attenuated in the subject P.

In FIG. 1, the image reconstituting unit 26 reads the coincidence counting information generated by the coincidence counting information generating unit 25 as projection data from the data storage unit 27, and performs a back projection process on the read-out projection data to reconstitute a PET image. Further, the image reconstituting unit 26 stores the reconstituted PET image in the data storage unit 27.

The system controlling unit 28 controls the operations of the gantry apparatus 10 and the console device 20, and thereby performs control of the entire PET apparatus. More specifically, the system controlling unit 28 controls the moving operation of the couch 12 and the process of collecting the counting information at the counting information collecting unit 15. Further, the system controlling unit 28 controls the process of generating the coincidence counting information at the coincidence counting information generating unit 25 and the process of reconstituting the PET image at the image reconstituting unit 26, based on the setting information input by the operator by way of the input unit 21. In addition, the system controlling unit 28 performs control so that the PET image stored in the data storage unit 27 is displayed on the display unit 22.

Then, after the reconstitution of the PET image, the system controlling unit 28 performs control so that all or part of the counting information is stored in the counting information storage unit 24. For example, the system controlling unit 28 performs control so that all the counting information including the counting information that is not adopted as coincidence counting information is maintained in the counting information storage unit 24. Alternatively, the system controlling unit 28 performs control so that the counting information except for the counting information instructed by the operator by way of the input unit 21 to abandon is maintained in the counting information storage unit 24.

Moreover, when receiving a request of changing the coincidence counting information generating conditions for generating the coincidence counting information after the reconstitution of the PET image, the system controlling unit 28 performs the following control. That is, the system controlling unit 28 controls the coincidence counting information generating unit 25 based on the changed coincidence counting information generating conditions so that the coincidence counting information is regenerated from the counting information stored in the counting information storage unit 24. Then, the system controlling unit 28 controls the image reconstituting unit 26 so that the PET image is reconstituted again by use of the coincidence counting information regenerated by the coincidence counting information generating unit 25.

For example, the system controlling unit 28 displays a GUI for inputting coincidence counting information generating conditions on the display unit 22, in response to an instruction from the operator. Then, the operator changes the coincidence counting information generating conditions, for example, indicated in FIG. 4A, by referring to the inputting GUI. The operator may change the time window width from "600 picoseconds" to "400 picoseconds". The changed coincidence counting information generating conditions are notified to the coincidence counting information generating unit 25 by way of the system controlling unit 28. Thus, the coincidence counting information generating unit 25 re-searches through the counting information illustrated in FIG. 3 for a combination of counting information items that agree with the changed coincidence counting information generating conditions, and generates the coincidence counting information. Then, the image reconstituting unit 26 reconstitutes, under the control of the system controlling unit 28, a new PET image by using the coincidence counting information regenerated by the coincidence counting information generating unit 25 as projection data. Thereafter, the PET image newly reconstituted by the image reconstituting unit 26 is displayed on the display unit 22 under the control of the system controlling unit 28.

When receiving a request to transfer the counting information stored in the counting information storage unit 24 to a storage medium, the system controlling unit 28 performs control so that the counting information stored in the counting information storage unit 24 is put into the storage medium. For example, at the time of maintenance of the like of the PET apparatus according to the first embodiment, the operator inputs by way of the input unit 21 a request to transfer the counting information stored in the counting information storage unit 24 in a detachable external storage medium such as a flexible disk drive (FD), a compact disc read only memory (CD-ROM), a magneto optical disk (MO), and a digital versatile disk (DVD). The system controlling unit 28 that receives the transfer request performs control so that the counting information stored in the counting information storage unit 24 is put into the storage medium.

Figure 5A:
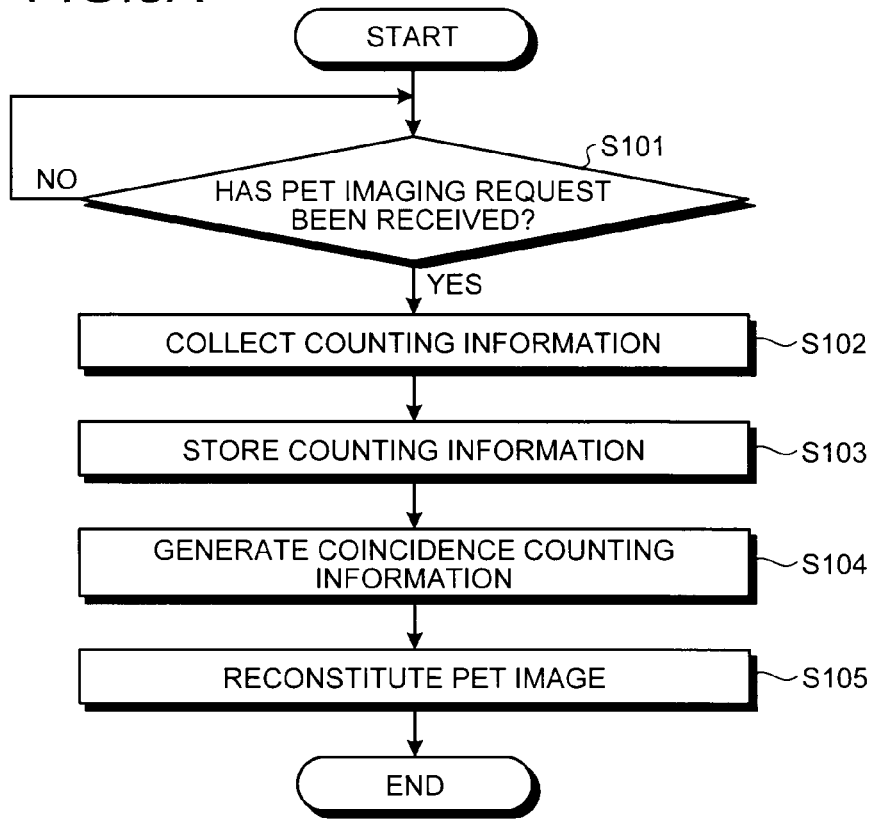
FIGS. 5A and 5B are flowcharts for explaining a process performed by the PET apparatus according to the first embodiment.
Figure 5B:
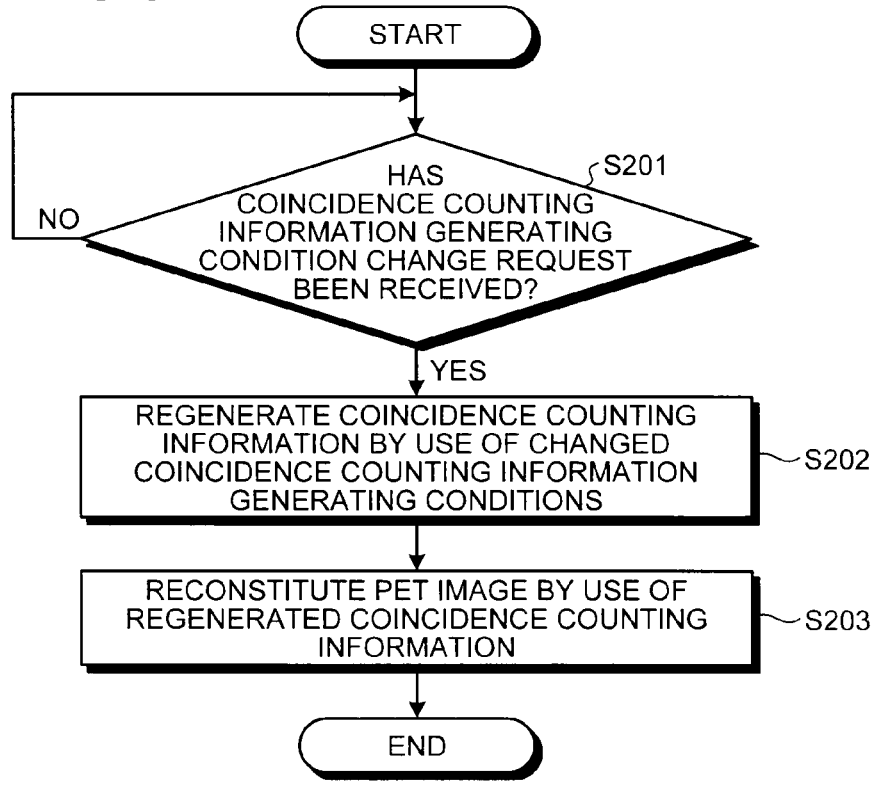

Next, the process performed by the PET apparatus according to the first embodiment is explained with reference to FIGS. 5A and 5B. FIGS. 5A and 5B are flowcharts for explaining the process of the PET apparatus according to the first embodiment.

As illustrated in FIG. 5A, the PET apparatus according to the first embodiment receives an imaging request for a PET image from the operator by way of the input unit 21 after carrying the subject P into the imaging space of the gantry apparatus 10 (yes at step S101), the counting information collecting unit 15 collects the counting information based on the counting results obtained by each detector module 14 during a predetermined monitoring period (step S102). In other words, the counting information collecting unit 15 collects, as counting information for each detector module 14, the detection position of the gamma ray detected by the detector modules 14, the energy value of the gamma ray at the incident time on the detector module 14, and the detection time of the gamma ray detected by the detector module 14, based on the counting results of the detector module 14.

Then, the counting information collecting unit 15 stores the collected counting information in the counting information storage unit 24 of the console device 20 (step S103). The coincidence counting information generating unit 25 searches, by referring to the detection times and the energy values of the counting information, for a combination of counting information items in which a difference in the detection times is within the time window width and each of the energy values is within the energy window width, and thereby generates the coincidence counting information (step S104).

Thereafter, the image reconstituting unit 26 performs a back projection process on the coincidence counting information generated by the coincidence counting information generating unit 25 as projection data and thereby reconstitutes a PET image (step S105), and the process is terminated. The system controlling unit 28 performs control so that all the counting information is put into the counting information storage unit 24 after the reconstitution of the PET image.

Then, as illustrated in FIG. 5B, when the PET apparatus according to the first embodiment receives a request of changing the coincidence counting information generating conditions from the operator (yes at step S201), the coincidence counting information generating unit 25 generates the coincidence counting information again under the control of the system controlling unit 28, in accordance with the changed coincidence counting information generating conditions (step S202).

Thereafter, under the control of the system controlling unit 28, the image reconstituting unit 26 reconstitutes a new PET image by use of the regenerated coincidence counting information (step S203), and the process is terminated.

When receiving a transfer request from the operator, the system controlling unit 28 performs control so that the counting information stored in the counting information storage unit 24 is put into a storage medium designated by the operator.

As explained above, according to the first embodiment, the counting information collecting unit 15 collects, as the counting information based on the counting results obtained by each photon-counting detector module 14 during the predetermined monitoring period, the detection position of the gamma ray detected by the detector module 14, the energy value of the gamma ray at the incident time on the detector modules 14, and the detection time of the gamma ray detected by the detector modules 14, and stores the collected counting information in the counting information storage unit 24 of the console device 20. The coincidence counting information generating unit 25 searches, by referring to, for example, the detection times and the energy values of the counting information, for a combination of counting information items in which a difference between the detection times falls within the time window width and each of the energy values is within the energy window width, and thereby generates the coincidence counting information. The image reconstituting unit 26 performs a back projection process on the coincidence counting information generated by the coincidence counting information generating unit 25 as projection data, and thereby reconstitutes a PET image. Then, after the reconstitution of the PET image, the system controlling unit 28 performs control so that all or part of the counting information is put into the counting information storage unit 24.

Thus, a conventional PET apparatus stores coincidence counting information that is generated only by the coincidence circuit provided as a hardware piece in the gantry apparatus 10, but the PET apparatus according to the first embodiment can store all the counting information of every detector module 14 in the console device 20, and generate coincidence counting information inside the console device 20 in accordance with a software program. In addition, the PET apparatus according to the first embodiment can hold the counting information collected during the time of taking a PET image even after the image is reconstituted.

Hence, according to the first embodiment, when the operator wishes to see a PET image that is reconstituted in accordance with different coincidence counting information generating conditions, the coincidence counting information generating unit 25 can immediately generate coincidence counting information based on the new coincidence counting information generating conditions, and quickly correct the PET image in accordance with the reader's request. Furthermore, a time-of-flight (TOF) PET apparatus that can accurately identify the emission position of gamma rays by use of a difference between the detection times of a pair of annihilation gamma rays has been developed. However, the time window width required for the TOF-PET is on the order of several hundred picoseconds. Because in a conventional PET apparatus, the signal transfer from the detector modules 14 to the coincidence circuit cannot exceed the speed of light, it is difficult to reconstitute a PET image on the TOF-PET.

However, with the PET apparatus according to the first embodiment, a detection time can be collected on the order of picoseconds as the counting information, and the coincidence counting information can be generated inside the console device 20. Thus, a PET image can be reconstituted by using a difference in detection times.

In addition, according to the first embodiment, when receiving a request to change the coincidence counting information generating conditions for generating the coincidence counting information after the reconstitution of the PET image, the system controlling unit 28 controls the coincidence counting information generating unit 25 so that the coincidence counting information is regenerated from the counting information stored in the counting information storage unit 24 in accordance with the changed coincidence counting information generating conditions. Then, the system controlling unit 28 controls the image reconstituting unit 26 so that a PET image is newly reconstituted by use of the coincidence counting information regenerated by the coincidence counting information generating unit 25. In other words, the PET apparatus according to the first embodiment is configured to automatically implement afresh the generation of the coincidence counting information and the reconstitution of the PET image when a request to change the coincidence counting information generating conditions is received. Thus, according to the first embodiment, the PET image can be quickly corrected in response to a reader's request.

According to the first embodiment, when receiving a request to transmit the counting information stored in the counting information storage unit 24 to a storage medium, the system controlling unit 28 performs control so that the counting information stored in the counting information storage unit 24 is put into the storage medium. Hence, even if, for example, the free space of the counting information storage unit 24 becomes short because of a high counting rate, the counting information is prevented from being abandoned according to the first embodiment.

According to the second embodiment, the storage of counting information in an X-ray CT apparatus that includes a photon-counting detector similar to the one adopted in the first embodiment is discussed.

The X-ray CT apparatus reconstitutes an X-ray CT image that shows morphological information of human body tissue of a subject by irradiating the subject with X rays from an X-ray tube and detecting the X rays that pass through the subject by a detector.

The X-ray CT apparatus according to the second embodiment adopts a photon-counting detector in place of a conventional current-mode measuring detector for counting of the X rays that pass through the subject to reconstitute an X-ray CT image. Then, the X-ray CT apparatus according to the second embodiment is configured to quickly correct the x-ray CT image in response to a reader's request.

The configuration of the X-ray CT apparatus according to the second embodiment is explained below with reference to FIG. 6 and the like. FIG. 6 is a diagram for explaining a configuration of an X-ray CT apparatus according to a second embodiment. As illustrated in FIG. 6, the X-ray CT apparatus according to the second embodiment includes a gantry apparatus 100, a couch 200, and a console device 30.

The gantry apparatus 100 irradiates the subject P with X rays and counts the X rays that pass through the subject P. The gantry apparatus 100 includes a high voltage generating unit 110, an X-ray tube 120, a detector 130, a counting information collecting unit 140, a rotation frame 150, and a gantry driving unit 160.

The rotation frame 150 is a ring-shaped frame that supports the X-ray tube 120 and the detector 130 in such a manner that they oppose each other across the subject P, and is rotated by the gantry driving unit 160 at a high speed on a circular path around the subject P.

The X-ray tube 120 is a vacuum tube that applies an X-ray beam to the subject P with a high voltage supplied by the high voltage generating unit 110 that is described later, and irradiates the subject P with the X-ray beam in accordance with the rotation of the rotation frame 150.

The high voltage generating unit 110 supplies a high voltage to the X-ray tube 120, the gantry driving unit 160 turns the X-ray tube 120 and the detector 130 on the circular path around the subject P by rotating the rotation frame 150.

The detector 130 is a photon-counting detector that conducts counting on the light derived from the X rays that pass through the subject P and thereby discriminates the energy value of the transmission X rays. For example, the detector 130 may have the same configuration as the detector modules 14 explained with reference to FIG. 2A according to the first embodiment.

The counting information collecting unit 140 collects the detection position of X rays detected by the detector 130 and the energy value at the incident time of the X rays onto the detector 130, as counting information, for each phase of the X-ray tube 120 (tube phase) from the counting results obtained by the detector 130, and sends the collected counting information to the console device 30 that is described later. For example, the counting information collecting unit 140 determines the detection position and the energy value with the same process as the one performed by the counting information collecting unit 15 according to the first embodiment.

The couch 200 is a device on which the subject P lies, and has a top plate 220 and a couch driving device 210. The top plate 220 is a plate on which the subject P is positioned, and the couch driving device 210 moves the top plate 220 in the Z-axis direction to carry the subject P into the rotation frame 150.

The console device 30 receives a manipulation of the X-ray CT apparatus by the operator, and also reconstitutes the X-ray CT image by use of the counting information collected by the gantry apparatus 100, and includes an input device 31, a display device 32, a scan controlling unit 33, a counting information storage unit 34, a preprocessing unit 35, an image reconstituting unit 36, an image storage unit 37, and a system controlling unit 38.

The input device 31 includes a mouse and a keyboard that the operator of the X-ray CT apparatus uses to input various instructions and settings, and sends the instructions and settings received from the operator to the system controlling unit 38. For example, the input device 31 receives from the operator the reconstituting conditions for reconstituting the X-ray CT image and the correction conditions for correcting the image.

The display device 32 is a monitor that the operator checks. Under the control of the system controlling unit 38, the display device 32 presents the X-ray CT image to the operator, and displays a graphical user interface (GUI) for receiving various instructions and settings from the operator by way of the input device 31.

The scan controlling unit 33 controls, under the control of the system controlling unit 38, the operations of the high voltage generating unit 110, the gantry driving unit 160, the counting information collecting unit 140, and the couch driving device 210, and thereby controls the process of collecting the counting information at the gantry apparatus 100.

The counting information storage unit 34 stores therein the counting information collected by the counting information collecting unit 140 for each tube phase. For example, the counting information storage unit 34 stores therein "P: P11, E: E11", "P: P12, E: E12" and the like as the counting information that is collected from the counting results obtained by the detector 130 in "tube phase: X1", as indicated in FIG. 7. FIG. 7 is a diagram for explaining the counting information storage unit according to the second embodiment, where "P" and "E" represent "scintillator number" and "energy value", respectively.

In a similar manner, the counting information storage unit 34 also stores therein, as illustrated in FIG. 7, the counting information collected from the counting results obtained the detector 130 in "tube phase: X2" and "tube phase: X3".

Figure 8:
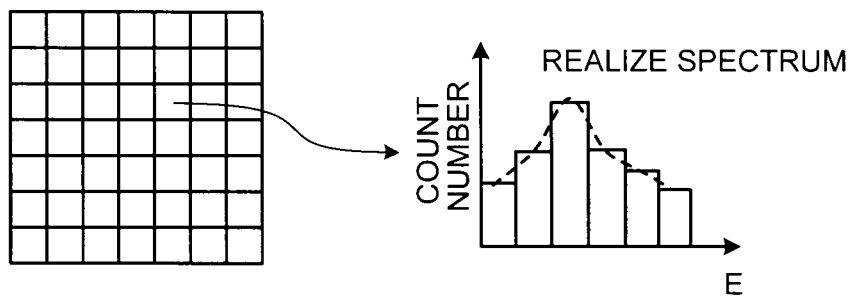
FIG. 8 is a diagram of characteristics of counting information according to the second embodiment.

In the counting information stored in the counting information storage unit 34, the energy values for different positions of the scintillator include the count number information for different energy values. In other words, as indicated in FIG. 8, the count number for each energy value is expressed in a histogram so that an energy spectrum can be reconstructed from which elements that constitute the human body tissue of the subject through which the X rays pass can be estimated. FIG. 8 is a diagram for explaining the characteristics of the counting information according to the second embodiment.

In FIG. 6, the preprocessing unit 35 performs a correction process, such as a logarithmic conversion process, an offset correction, a sensitivity correction, a beam hardening correction onto the counting information stored in the counting information storage unit 34, and thereby generates the projection data. The correction conditions for the correction process can be arbitrarily changed by the operator.

The image reconstituting unit 36 reconstitutes the X-ray CT image by performing a back projection process on the projection data generated by the preprocessing unit 35 from the counting information, and stores the reconstituted X-ray CT image in the image storage unit 37. In other words, the image reconstituting unit 36 reconstitutes the X-ray CT image that describes differences in element level in detail, by use of the projection data generated from the counting information that reproduces the spectrum of elements.

The system controlling unit 38 controls the operations of the gantry apparatus 100, the couch 200 and the console device 30, and thereby performs control of the entire X-ray CT apparatus. More specifically, the system controlling unit 38 controls the scan controlling unit 33 to collect the counting information from the gantry apparatus 100. In addition, the system controlling unit 38 controls the preprocessing unit 35 and the image reconstituting unit 36 to control the image reconstituting process of the console device 30. Moreover, the system controlling unit 38 performs control so that an X-ray CT image stored in the image storage unit 37 is displayed on the display device 32.

Then, the system controlling unit 38 performs control so that all or part of the counting information is maintained in the counting information storage unit 34 after the reconstitution of the X-ray CT image.

Furthermore, when receiving a request of changing the image reconstituting conditions after the reconstitution of the X-ray CT image, the system controlling unit 38 performs the following controlling process. The reconstituting conditions are, for example, correction conditions for the correction process performed by the preprocessing unit 35. In other words, when receiving a request to change the correction conditions after the reconstitution of the X-ray CT image, the system controlling unit 38 controls the preprocessing unit 35 in accordance with the changed correction conditions so that projection data is regenerated from the counting information stored in the counting information storage unit 34. Then, the system controlling unit 28 controls the image reconstituting unit 36 by use of the projection data regenerated by the preprocessing unit 35 to newly reconstitute the X-ray CT image. Then, the X-ray CT image newly reconstituted by the image reconstituting unit 36 is displayed on the display device 32 under the control of the system controlling unit 38.

When receiving a request to transmit the counting information stored in the counting information storage unit 34 to a storage medium, the system controlling unit 38 performs control so that the counting information stored in the counting information storage unit 34 is stored in the storage medium.

Figure 9:
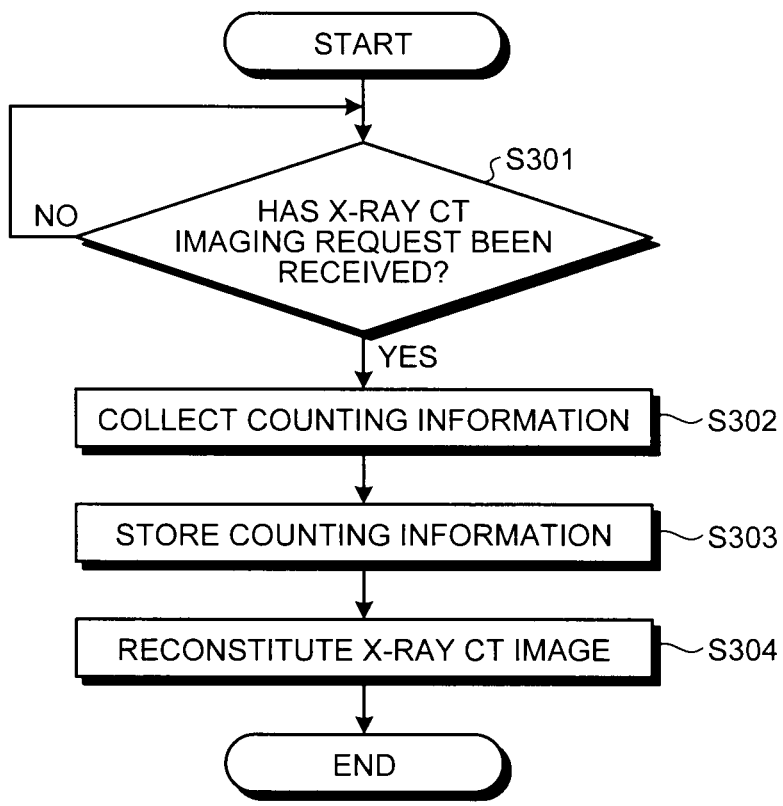
FIG. 9 is a flowchart of the X-ray CT apparatus according to the second embodiment.

Next, the process procedure followed by the X-ray CT apparatus according to the second embodiment is explained with reference to FIG. 9. FIG. 9 is a flowchart for explaining the process performed by the X-ray CT apparatus according to the second embodiment.

As illustrated in FIG. 9, when the X-ray CT apparatus according to the second embodiment carries the subject P into the rotation frame 150 of the gantry apparatus 100 and then receives a request to take an X-ray CT image from the operator by way of the input device 31 (yes at step S301), the counting information collecting unit 140 collects the counting information, based on the counting results obtained by the detector 130 (step S302). In other words, the counting information collecting unit 140 collects, as the counting information, the detection position of the transmitted x rays detected by the detector 130 and the energy value of the transmitted x rays at the incident time onto the detector 130, for each tube phase of the x-ray tube 120.

Thereafter, the counting information collecting unit 140 stores the collected counting information into the counting information storage unit 34 of the console device 30 (step S303), the image reconstituting unit 26 reconstitutes the X-ray CT image by performing the back projection process onto the projection data generated by the preprocessing unit 35 from the counting information (step S304), and the process is terminated.

As discussed above, the counting information collecting unit 140 according to the second embodiment collects, as counting information prepared from the counting results obtained by the photon-counting detector 130, the detection position of the transmitted X rays detected by the detector 130 and the energy value of the transmitted X rays at the incident time onto the detector 130, for each tube phase of the x-ray tube 120, and stores the collected counting information into the counting information storage unit 34 of the console device 30. The preprocessing unit 35 generates projection data by performing various correction processes onto the counting information stored in the counting information storage unit 34, and the image reconstituting unit 36 reconstitutes the X-ray CT image by performing a back projection process onto the projection data generated by the preprocessing unit 35. Then, after the reconstitution of the X-ray CT image, the system controlling unit 38 performs control so that all or part of the counting information is put into the counting information storage unit 34.

Hence, according to the second embodiment, the counting information is stored inside the console device 30, and even after the X-ray CT image is reconstituted, the counting information that is collected during the X-ray CT imaging time period can be maintained. Thus, according to the second embodiment, when the operator wishes to consult an X-ray CT image reconstituted in accordance with different correction conditions, the projection data can be immediately regenerated at the preprocessing unit 35 based on the new correction conditions, and the X-ray CT image can be quickly corrected in response to the reader's request.

In addition, according to the second embodiment, when a request to change the image reconstituting conditions (correction conditions) is received after the reconstitution of the X-ray CT image, the system controlling unit 38 controls the preprocessing unit 35 so that projection data is regenerated from the counting information stored in the counting information storage unit 34 in accordance with the changed correction conditions. Then, the system controlling unit 28 controls the image reconstituting unit 36 to newly reconstitute the X-ray CT image by use of the projection data regenerated by the preprocessing unit 35. In other words, the system of the X-ray CT apparatus according to the second embodiment is configured to automatically re-execute the generation of the projection data and the reconstitution of the X-ray CT image when a request to change the correction conditions that are image reconstituting conditions is received. Thus, according to the second embodiment, the X-ray CT image can be further quickly corrected in response to the reader's request.

In addition, according to the second embodiment, when a request to transmit the counting information stored in the counting information storage unit 34 to a storage medium is received, the system controlling unit 38 performs control so that the counting information stored in the counting information storage unit 34 is put into the storage medium. Hence, according to the second embodiment, the counting information is prevented from being abandoned due to free space that becomes short in the counting information storage unit 24.

As explained above, according to the first and second embodiments, medical images reconstituted by use of radiation can be quickly corrected in response to the reader's request.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation diagnostic apparatus, comprising:
   a photon-counting detector that performs counting of light derived from radiation that is incident;
   a counting information storage unit that stores therein at least a detection time of the radiation, as counting information based on a counting result obtained by the detector;
   a coincidence counting information generating unit that generates coincidence counting information based on the detection time in the counting information;
   an image reconstituting unit that reconstitutes a medical image by use of the coincidence counting information; and
   a controlling unit that performs control so that all or part of the counting information is put into the counting information storage unit,
   wherein the controlling unit is configured to change coincidence counting information generating conditions for generating the coincidence counting information based on the counting information stored in the counting information storage unit.

2. The radiation diagnostic apparatus according to claim 1, wherein, when a transmission request to transmit the counting information stored in the counting information storage unit to a storage medium is received, the controlling unit performs the control so that the counting information stored in the counting information storage unit is put into the storage medium.

3. The radiation diagnostic apparatus according to claim 1, wherein:
the detector performs the counting on light derived from radiation emitted from positron emitting radionuclides that are introduced to a subject;
the counting information storage unit stores therein, as the counting information, a detection position of the radiation detected by the detector, an energy value of the radiation at an incident time onto the detector, and the detection time of the radiation; and
the coincidence counting information generating unit that searches, based at least on the detection time in the counting information stored in the counting information storage unit, for a combination of items of the counting information in which a pair of radiation beams emitted from the positron emitting radionuclide are coincidentally counted, and generates the coincidence counting information that is the combination of the items of the counting information that are searched for and found.

4. The radiation diagnostic apparatus according to claim 1, wherein, when a change request to change coincidence counting information generating conditions for generating the coincidence counting information is received, the controlling unit controls the coincidence counting information generating unit so that coincidence counting information is regenerated from the counting information stored in the counting information storage unit in accordance with the coincidence counting information generating conditions that are changed, and controls the image reconstituting unit so that a medical image is newly reconstituted by use of the coincidence counting information regenerated by the coincidence counting information generating unit.

5. The radiation diagnostic apparatus according to claim 4, wherein the controlling unit receives the change request to change the coincidence counting information generating conditions after the medical image is reconstituted.

6. The radiation diagnostic apparatus according to claim 1, wherein the controlling unit controls so that, after the medical image is reconstituted, the all or part of the counting information is put into the counting information storage unit.

7. An image reconstructing method, comprising:
performing counting with a photon-counting detector on light derived from radiation that is incident thereon;
storing at least a detection time of the radiation, as counting information in a counting information storage unit based on a counting result obtained by the detector;
generating coincidence counting information based on the detection time in the counting information at a coincidence counting information generating unit;
reconstituting a medical image by use of the coincidence counting information at an image reconstituting unit; and
performing control at a controlling unit so that all or part of the counting information is stored in the counting information storage unit,
wherein the controlling unit is configured to change coincidence counting information generating conditions for generating the coincidence counting information based on the counting information stored in the counting information storage unit.

8. The image reconstructing method according to claim 7, wherein, when a transmission request to transmit the counting information stored in the counting information storage unit to a storage medium is received, the controlling unit performs control so that the counting information stored in the counting information storage unit is put into the storage medium.

9. The image reconstructing method according to claim 7, further comprising:
performing at the detector the counting on light derived from radiation emitted from positron emitting radionuclides that are introduced to a subject;
storing in the counting information storage unit a detection position of the radiation detected by the detector, an energy value of the radiation at an incident time onto the detector, and the detection time of the radiation, as the counting information; and
searching, at the coincidence counting information generating unit, for a combination of items of the counting information in which a pair of radiation beams emitted from the positron emitting radionuclides are coincidentally counted, based on at least the detection time in the counting information stored in the counting information storage unit, and generating the coincidence counting information that is the combination of the items of the counting information that is searched for and found.

10. The image reconstructing method according to claim 7, wherein, when a change request to change coincidence counting information generating conditions for generating the coincidence counting information is received, the controlling unit controls the coincidence counting information generating unit so that coincidence counting information is regenerated from the counting information stored in the counting information storage unit in accordance with the coincidence counting information generating conditions that are changed, and controls the image reconstituting unit so that a medical image is newly reconstituted by use of the coincidence counting information regenerated by the coincidence counting information generating unit.

11. The image reconstructing method according to claim 10, wherein the controlling unit receives the change request to change the coincidence counting information generating conditions after the medical image is reconstituted.

12. The image reconstructing method according to claim 7, wherein the controlling unit controls so that, after the medical image is reconstituted, the all or part of the counting information is put into the counting information storage unit.

* * * * *